US009650311B2

(12) United States Patent
Coupard et al.

(10) Patent No.: US 9,650,311 B2
(45) Date of Patent: May 16, 2017

(54) PROCESS FOR PURIFICATION OF $CO_2$ IN AN ETHYLENE STREAM OBTAINED FROM THE DEHYDRATION OF ETHANOL

(71) Applicants: IFP Energies nouvelles, Rueil-Malmaison Cedex (FR); Total Research & Technology Feluy, Seneffe (BE)

(72) Inventors: Vincent Coupard, Villeurbanne (FR); Thomas Plennevaux, Lyons (FR); Stephanie Fleurier, Lyons (FR); Walter Vermeiren, Houthalen-Helchteren (BE); Delphine Minoux, Nivelles (BE); Philip De Smedt, Sint-Niklaas (BE); Cindy Adam, Wierde (BE); Nikolai Nesterenko, Nivelles (BE)

(73) Assignees: TOTAL RESEARCH & TECHNOLOGY FELUY, Seneffe (BE); IFP ENERGIES NOUVELLES, Rueil-Malmaison (FR)

( * ) Notice: Subject to any disclaimer, the term of this patent is extended or adjusted under 35 U.S.C. 154(b) by 27 days.

(21) Appl. No.: 14/760,827

(22) PCT Filed: Jan. 10, 2014

(86) PCT No.: PCT/FR2014/050043
§ 371 (c)(1),
(2) Date: Jul. 14, 2015

(87) PCT Pub. No.: WO2014/108647
PCT Pub. Date: Jul. 17, 2014

(65) Prior Publication Data
US 2015/0353443 A1    Dec. 10, 2015

(30) Foreign Application Priority Data
Jan. 14, 2013    (FR) ..................................... 13 00066

(51) Int. Cl.
*C07C 1/24*    (2006.01)

(52) U.S. Cl.
CPC ..................................... *C07C 1/24* (2013.01)

(58) Field of Classification Search
CPC .... C07C 1/24; C07C 1/00; C07C 1/20; C07C 11/04; C07C 11/02; C07C 7/11; C07C 7/04; C07C 7/005
(Continued)

(56) References Cited

U.S. PATENT DOCUMENTS

| 2013/0172654 A1 | 7/2013 | Avaullee et al. |
| 2013/0178683 A1 | 7/2013 | Avaullee et al. |
| 2015/0291488 A1* | 10/2015 | Kloth ........................ C07C 1/20 585/640 |

FOREIGN PATENT DOCUMENTS

| WO | 2007/134415 A2 | 11/2007 |
| WO | 2011/076752 A1 | 6/2011 |

OTHER PUBLICATIONS

International Search Report dated Sep. 16, 2014 issued in corresponding PCT/FR2014/050043 application (pp. 1-2).

* cited by examiner

*Primary Examiner* — Sharon Pregler
(74) *Attorney, Agent, or Firm* — Millen White Zelano and Branigan, PC; John Sopp; Anthony Zelano

(57) ABSTRACT

Process for the production of ethylene from an ethanol feedstock that comprises these stages:
a) dehydration to produce at least ethylene and water effluents,
b) partial condensation of said ethylene effluent,
c) separating phases of said partially condensed ethylene effluent to produce gas and liquid effluents,
d) compression of said gas effluent to produce compressed gas effluent,
e) washing said compressed gas effluent by contact with the recycled washing water of stage h) to produce washed gas and waste water effluents,
f) absorption of said washed gas effluent by contact with at least an absorbent solution to produce purified gas effluent, (Continued)

g) distilling said waste water effluent and, jointly, said water effluent from said dehydration stage to produce at least gas distillate, liquid distillate, purified water effluent, and distillation residue, h) recycling, as washing water, at least a portion of said purified water effluent upstream from the washing stage e).

10 Claims, 2 Drawing Sheets

PROCESS FOR PURIFICATION OF $CO_2$ IN AN ETHYLENE STREAM OBTAINED FROM THE DEHYDRATION OF ETHANOL

FIELD OF THE INVENTION

This invention relates to a process that makes it possible to eliminate the $CO_2$ from the ethylene stream that is obtained from the reactors for the process of dehydration of ethanol. This invention relates in particular to the case where the concentration of $CO_2$ is too great to make it possible to reasonably consider the solution of adsorption on a capture mass.

PRIOR ART

The patent application WO2013/014002 A1 describes the purification section (after drying) of an ethylene stream comprising at most 1% by weight of oxidized compounds (alcohols, diethyl ether, acids, etc.), of ethane, CO, $CO_2$, $H_2$, $CH_4$ and $C_3+$. The patent describes the distillation stages making it possible to separate ethane, oxidized compounds, and $C_3^+$. It describes in particular a solution for separation of $CO_2$ using a selective adsorption mass. Finally, it describes a distillation making it possible to separate the last impurities from the ethylene stream.

This patent explains that the separation of $CO_2$ using a soda tower makes it necessary to separate acetaldehyde upstream (possible clogging of the absorber with soda due to the basic polymerization of the acetaldehyde), contrary to the solution of adsorption that is simpler to use.

This patent does not mention the maximum concentration of $CO_2$ in the unpurified ethylene stream. Only the overall concentrations of impurities are mentioned.

The U.S. Pat. No. 6,459,009 relates to a process for dehydration of alcohol in a fluidized bed. It describes a thermal integration and purification solution that uses two consecutive columns for quenching with water. The first column makes it possible to separate water from the effluent and to recover the heat that makes it possible to preheat the feedstock of the process. The second column makes it possible to obtain purified water that is recycled in the first column and a stream of olefins comprising between 10 ppm by weight and 10% by weight of oxidized compounds. This patent relates to the processes for dehydration of oxidized compounds in general but mentions the reaction for dehydration of methanol into olefin (Methanol To Olefin, or MTO according to the English designation), for example: the MTO reaction being exothermic whereas that of this invention is endothermic, with the application of one to the other not being obvious. Neither the separation of $CO_2$ nor the possibility of having a compression zone between the two quenching stages is mentioned.

The patent application WO 2011/076752 describes a separation of the oxidized compounds in a hydrocarbon stream. It cites the olefins that are obtained from the dehydration of methanol, for example. This patent describes the use of an absorption column using a solvent that is capable of collecting water and oxidized compounds (for example, glycols, amines). This solvent is regenerated by stripping or distillation. The stream that comprises the oxidized compounds is washed with water so as to separate from it, on the one hand, the oxidized compounds, and, on the other hand, a stream that can be recycled in the reaction section that comprises 10% oxidized compounds.

This patent then describes the separation of the oxidized compounds remaining in the gaseous phase of absorption by washing with soda making it possible to eliminate the acid components.

The described process has the drawback of using two washing columns and of introducing a third element (the solvent). It does not mention the separation of the $CO_2$, with this effect, however, being induced by the presence of the soda column.

To our knowledge, there is no document relating to a solution for treatment of an ethylene stream charged with $CO_2$ that is obtained from a reaction section for dehydration of ethanol using a single water washing column followed by a $CO_2$ absorption column using a chemical or physical solvent.

SUMMARY AND ADVANTAGE OF THE INVENTION

The invention relates to a process for the production of ethylene from an ethanol feedstock that comprises at least the following stages:

a) A stage for dehydration of a dehydration feedstock comprising said ethanol feedstock in such a way as to produce at least an ethylene effluent and at least a water effluent, b) A stage for partial condensation of said ethylene effluent by heat exchange with at least a cold source at a temperature of between 20 and 50° C., c) A stage for separation of phases of said partially condensed ethylene effluent in such a way as to produce a gas effluent and a liquid effluent, d) A stage for compression of said gas effluent that is obtained from stage b) in such a way as to produce a compressed gas effluent followed by a cooling to a temperature of between 10 and 50° C., e) A stage for washing by bringing said compressed gas effluent into contact with the recycled washing water according to stage h) in a washing column in such a way as to produce a washed gas effluent and a waste water effluent, f) A stage for absorption by bringing said washed gas effluent into contact with at least an absorbent solution in an absorption column, with said absorbent solution comprising at least a solvent that is selected from among the group that consists of the chemical and physical solvents, in such a way as to produce a purified gas effluent and a waste absorbent solution effluent, g) A stage for distillation of said waste water effluent that is obtained from stage e), and, jointly, said water effluent that is obtained from said dehydration stage in such a way as to produce at least a gas distillate, a liquid distillate, a purified water effluent, and a distillation residue, h) A stage for recycling at least a portion of said purified water effluent that is obtained from stage g) upstream from the washing stage e), with said portion then being referred to as washing water.

The commercial specifications of polymer-grade ethylene impose a maximum concentration of $CO_2$ of 0.5 ppm by volume.

One advantage of this invention is to make it possible to increase the flexibility of the dehydration process by increasing the acceptable quantity of $CO_2$ in the effluent from the reactor. Another advantage of this invention is to limit the equipment that is necessary for the purification of the dehydration effluent by integrating the purification of the washing water and the water for dilution of the reaction in a single distillation. This invention makes it possible in addition to avoid the presence of equipment and the consumption of utilities dedicated to the implementation and the regeneration of capture masses of $CO_2$.

DESCRIPTION OF THE INVENTION

This invention relates to the treatment of an ethylene effluent that is obtained from a stage for dehydration of ethanol. The reaction for dehydration of alcohols is accompanied by the formation of $CO_2$, whose concentration in the effluent can vary based on, for example, the quality of the feedstock, the operating conditions, and the catalyst.

Feedstock

In accordance with the invention, the feedstock that is treated in the dehydration process is an ethanol feedstock.

Said ethanol feedstock is advantageously a concentrated hydrated ethanol feedstock. Concentrated hydrated ethanol feedstock is defined as an ethanol feedstock comprising a percentage by mass of ethanol that is greater than or equal to 35% by weight. Preferably, said concentrated hydrated ethanol feedstock comprises a percentage by mass of ethanol of between 35 and 99.7% by weight.

Said ethanol feedstock also advantageously comprises, in addition to water, a content of alcohols other than ethanol, such as, for example, methanol, butanol, and/or isopentanol, that is less than 10% by weight, and preferably less than 5% by weight, a content of oxidized compounds other than alcohols, such as, for example, ethers, acids, ketones, aldehydes and/or esters, that is less than 1% by weight, and a content of nitrogen and sulfur, organic and mineral, that is less than 0.5% by weight, with the percentages by weight being expressed relative to the total mass of said feedstock.

Said treated ethanol feedstock is optionally obtained by an alcohol synthesis process starting from fossil resources such as, for example, from carbon, natural gas, or carbon-containing wastes.

Said ethanol feedstock can also advantageously be obtained from non-fossil resources. Preferably, the ethanol feedstock that is treated in the process according to the invention is an ethanol feedstock that is produced from renewable sources that are obtained from the biomass, often called "bioethanol." The bioethanol is a feedstock that is produced by biological means, preferably by fermentation of sugars obtained from, for example, sugar-producing crops such as sugarcane (saccharose, glucose, fructose, and sucrose), beet scraps, or else amylase plants (starch) or lignocellulosic biomass or hydrolyzed cellulose (majority glucose and xylose, galactose), containing variable quantities of water.

For a more complete description of the standard fermentation processes, it is possible to refer to the work "Les Biocarburants, État des lieux, perspectives et enjeux du développement [The Biofuels, Assessment, Perspectives and Development Issues]," Daniel Ballerini, Editions Technip.

Said ethanol feedstock can also advantageously be obtained from synthesis gas.

Said ethanol feedstock can also, advantageously also, be obtained by hydrogenation of the corresponding acids or esters. In this case, the acetic acid or the acetic esters are advantageously hydrogenated into ethanol by hydrogen. The acetic acid can advantageously be obtained by carbonylation of methanol or by fermentation of carbohydrates.

Dehydration Stage a)

In accordance with the invention, a dehydration feedstock that comprises said ethanol feedstock undergoes a stage a) for dehydration in a reaction section by following a technology that is known by one skilled in the art, as described in, for example, the documents U.S. Pat. No. 4,396,789, WO 2011/002699, and WO 2007/134415 or any other technology for catalytic dehydration of ethanol into ethylene.

Said dehydration feedstock also advantageously comprises an addition of water that consists of the dilution water that is obtained from stage h) for recycling and/or a stream of water from a source that is external to the process.

This addition of water makes it possible to compensate for the purging that is conventionally carried out on the recycling of the dilution water when the process comprises such a recycling, whose partial flow of water would be greater than the quantity of water produced in the reaction section. Actually, it may be advantageous to increase the purging of the process, for example, for eliminating an abnormally high quantity of salts obtained from the ethanol feedstock. This option makes it possible to treat dirtier ethanol feedstocks (charged with salts, ashes . . . ) than the one considered for the design of the unit.

Said dehydration stage a) produces at least an ethylene effluent and at least a water effluent.

Said dehydration feedstock is evaporated in an evaporator. After passing into the evaporator, an unevaporated fraction may remain. This fraction, liquid, is evacuated and constitutes said water effluent.

The fraction of the dehydration feedstock that is evaporated in the evaporator is then advantageously heated and/or compressed under the temperature and pressure conditions of the dehydration reaction.

The water effluent contains an unreacted ethanol fraction that will be recycled after purification in stage g), a fraction of dilution water, and advantageously the ashes and other impurities contained in ethanol. This water effluent can also contain a fraction of other oxidized compounds, for example the diethyl ether that is obtained from a pretreatment stage or other heavy alcohols.

Said ethylene effluent (excluding water) can contain up to 10,000 ppm by volume of $CO_2$ and up to 15,000 ppm by volume of acetaldehyde.

Partial Condensation Stage b)

In accordance with the invention, said ethylene effluent that is obtained from the dehydration stage a) undergoes a cooling followed by a partial condensation by heat exchange with at least a cold source.

In this stage of the process and those that follow, all of the streams that contain liquid water and acids can advantageously be neutralized using an aqueous soda solution. The pH of the neutralized solution is to be greater than 7 and advantageously between 7 and 9.

Preferably, the dehydration feedstock is used as one of these cold sources.

The exchanger thus makes it possible to condense between 50 and 95% by weight of the acetaldehyde, preferably between 60 and 80% by weight. This arrangement according to the invention therefore thus considerably limits the quantity of acetaldehyde that has to be treated during stage e).

The temperature of the ethylene effluent that is partially condensed at the end of stage b) is selected to be low enough so that the major portion of the acetaldehyde that is in said partially condensed ethylene effluent is separated in said liquid effluent. The operating pressure of stage c) corresponds to that of the dehydration stage a) minus the pressure drops between the two stages. It lies between 0.2 and 1.1 MPa, preferably between 0.4 and 0.8 MPa.

The exchange of heat with said cold source is such that the temperature of the partially condensed ethylene effluent that is obtained from the partial condensation stage b) is between 20 and 50° C., preferably between 25 and 45° C.

Phase Separation Stage c)

In accordance with the invention, the ethylene effluent that is partially condensed during stage b) then undergoes a phase separation stage in such a way as to produce a gas effluent and a liquid effluent.

Compression Stage d)

Said gas effluent that is obtained from the phase separation stage c) then undergoes a compression stage in such a way as to produce a compressed gas effluent. Said compression can be carried out by any means known to one skilled in the art, for example by using a centrifugal or volumetric compressor, optionally comprising several stages with intermediate cooling.

The liquid fraction that is optionally condensed during the compression advantageously undergoes a distillation stage g).

Said compression stage makes it possible to bring said compressed gas effluent to a pressure that is sufficient for allowing the purification stages e), f) and g) and whose operating pressure is directly dependent upon this compressor, aside from the pressure drops. Said pressure is between 1.1 and 5.1 MPa, preferably between 1.6 and 3.6 MPa.

Said compressed gas effluent is then cooled by heat exchange with a cold source for reaching a temperature of between 10 and 50° C., advantageously between 15 and 50° C., preferably between 25 and 45° C. This temperature is selected to be the lowest possible in such a way as to facilitate the washing stage e) by solvation of oxidized compounds.

Washing Stage e)

In accordance with the invention, said cooled compressed gas effluent then undergoes a washing stage by being brought into contact with the washing water in a washing column in such a way as to produce a washed gas effluent and a waste water effluent.

Said washing stage makes it possible to separate the oxidized compounds (ethers, acids, aldehydes, alcohols) of said cooled compressed gas effluent. In particular, said washing stage makes it possible to bring the acetaldehyde concentration below 150 ppm by weight, preferably below 100 ppm by weight. Actually, the acetaldehyde polymerizes in a basic medium for providing oils (red oils, polyacetaldehydes) leading at a minimum to a deterioration of the washing performance and over time to the inoperability of the column, for example because of a clogging of the plates or packing.

Said washing stage is used in a washing column comprising internals that are selected from among the structured packings, the plates, or any other technology for bringing into contact a gas and a liquid known by one skilled in the art.

Said washing water comprises water, advantageously mixed with ethanol so as to facilitate the solubilization of oxidized compounds and potentially supplemented with stabilizing agents (bisulfites) or antioxidants (heavy alcohols, phenols, BHT). The washing of oxidized compounds is all the more effective since the temperature is low (solvation promoted at low temperature) and since the ethanol fraction in the washing water is high. This ethanol fraction in the washing water is between 0 and 50% by weight, preferably between 0 and 10% by weight.

Said washing stage is performed at a temperature of between 10 and 50° C., advantageously between 15 and 50° C., preferably between 25 and 45° C., with said temperature being adjusted during stage d) for supplying the column and during stage h) for the washing fluid. Said temperature is selected to be the lowest possible based on available utilities, with the restriction of remaining higher than the temperature for forming hydrates. A temperature that is higher than 10° C., advantageously higher than 15° C., and preferably higher than 25° C. will be taken.

Preferably, said waste water effluent is treated in the distillation stage g) in such a way as to separate the oxidized compounds and to make possible the recycling of the washing water. In the case where the concentration of oxidized compounds (in particular of acetaldehyde) in said waste water effluent is low, i.e., at least less than the concentration of oxidized compounds in the ethylene effluent of the dehydration stage a), a fraction of said waste water effluent can advantageously be recycled directly upstream from the dehydration stage a).

Absorption Stage f)

The $CO_2$ is finally separated owing to an absorption column using a solvent. The gas is purified by contact with the absorbent solution, and then the absorbent solution is regenerated thermally. The composition of the absorbent solution is selected for its capacity to absorb the acid compounds without interaction with the matrix (olefin).

In accordance with the invention, said washed gas effluent undergoes an absorption stage by the contact in an absorption column with at least an absorbent solution in such a way as to produce a purified gas effluent and a waste absorbent solution effluent. Said absorption stage makes it possible to separate the $CO_2$.

The temperature of the absorbent solution(s) entering the absorption stage f) is between 25 and 50° C. The temperature of the washed gas effluent is the temperature of said effluent exiting the washing stage e).

The absorbent solution comprises a solvent that is selected from among the chemical solvents and the physical solvents.

The chemical solvents are selected from among the soda and the amines that are selected from among MEA (monoethanolamine), DEA (diethanolamine), MDEA (methyl diethanolamine), DIPA (diisopropylamine), DGA (diglycolamine), diamines, piperazine, and hydroxyethyl piperazine, taken by themselves or in combination, for example in a mixture of one or more tertiary amines with one or more primary or secondary amines. If the selected chemical solvent comprises soda, the absorbent solution comprises between 10 and 50% by weight of soda in aqueous solution. If the selected chemical solvent comprises amines, it comprises in general between 10% and 80%, preferably between 20% and 60%, by weight of amines, preferably alkanolamines and comprising at least 20% by weight of water, preferably at least 40% by weight of water.

The physical solvents are selected from among N-formyl morpholine, ethers of glycols, sulfolane, and thiodiethanol. The physical solvent can be mixed with one or more chemical solvents mentioned above and/or with water.

Said waste absorbent solution effluent can be neutralized or recycled. In the case of the recycling of the waste absorbent solution effluent, optionally after purification and/or regeneration of said waste absorbent solution effluent, an addition of fresh absorbent solution can be carried out, so as to compensate for the losses of absorbent solution in the different phases of stage f).

For example, the soda will be neutralized, and fresh soda will be imported for supplying said absorption stage f). In the case where the solvent is an amine or a physical solvent, it can be treated again and recycled (ex situ or in situ).

Said purified gas effluent is then advantageously compressed and then directed toward purification stages; for example, it will undergo a drying followed by one or more cryogenic distillation(s) that will make it possible to bring the purified gas effluent to the desired specifications for ethylene. This effluent is the main product of the process according to the invention.

In an optional manner, a capture mass (which can be regenerated or not) of the $CO_2$ can advantageously be installed at the end of the chain so as to eliminate all of the last traces of $CO_2$ and optionally to reduce the treatment cost of the chemical or physical solvent.

Distillation Stage g)

In accordance with the invention, said water effluent that is obtained from stage a), said liquid effluent that is obtained from stage c), and said waste water effluent that is obtained from stage e) undergo a distillation stage in a distilling column in such a way as to produce at least four fractions: a vapor distillate, a liquid distillate, an intermediate draw-off, called a purified water effluent, for the most part containing water, unreacted ethanol that is condensed in the phase separation stage c), as well as ethanol in the water effluent that is obtained from the dehydration stage a), and a distillation residue, composed of water and neutralization residue salts or contained in the alcohol that is under consideration. Said distillation residue represents the purging of the process, and its partial water flow rate corresponds to the water flow rate formed by the dehydration reaction.

The liquid fraction that is optionally condensed during the compression stage d) also advantageously undergoes the distillation stage g).

Said vapor distillate and liquid distillate contain for the most part the acetaldehyde that is extracted in the washing stage e) (10) and a fraction of ethanol, ethylene, and water.

The operating conditions and the sizing of the column are such that the losses of ethanol and ethylene are the lowest possible. The minimization of the ethylene losses leads to having a significant external reflux, between 1 and 10 times the total flow rate of the liquid and vapor distillates, preferably between 3 and 7 times. The external reflux corresponds to the liquid stream that is obtained from the reflux flask and recycled at the head of the distillation column.

Said distilling column is operated at a pressure of between 0.2 MPa and 1.1 MPa, preferably between 0.2 MPa and 0.4 MPa.

Said distilling column can advantageously be a column with an inside wall (dividing wall column in English).

The temperature of the bottom of said column is between 80 and 160° C., preferably between 100 and 150° C., and even more preferably between 120 and 140° C. The temperature of the reflux flask of said column is between 20 and 50° C., preferably between 25 and 45° C.

Recycling Stage h)

In accordance with the invention, said purified water effluent is divided into two: a portion corresponding to the necessary washing water flow rate in the washing stage e) is cooled by heat exchange with a cold source and recycled upstream from the washing stage e). Said portion is referred to as washing water.

The other portion, referred to as dilution water, is advantageously recycled upstream from the dehydration stage a) in such a way as to serve as a thermal diluent. In the case where the dehydration stage a) partially converts ethanol, the dilution water contains diethyl ether, unconverted at the end of the dehydration stage a) (case of dehydration processes with low conversion per pass).

In accordance with common practice during recycling, a purge is advantageously carried out in the recycling of washing water and/or dilution water.

Figure 1:
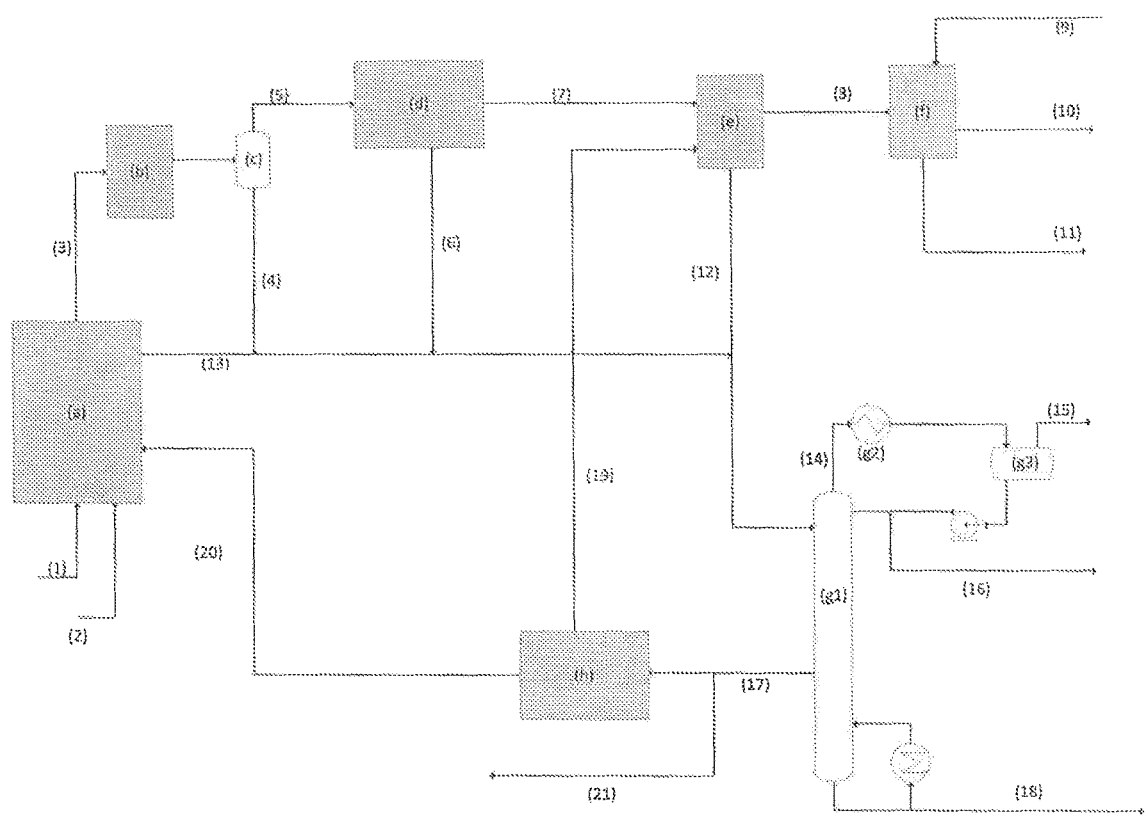
FIG. 1 shows a possible arrangement of the process according to the invention.

The ethanol feedstock (1), the dilution water (20), and a stream of water external to the process (2) supply the dehydration stage (a). The water effluent (13) is directed toward the distillation stage (g). The ethylene effluent (3) that is obtained from the dehydration stage (a) undergoes a partial condensation stage (b). The effluent from this condenser is brought into a phase separation stage (c), where a gas effluent (5) and a liquid effluent (4) are separated.

The gas effluent (5) that is obtained from stage (c) then undergoes a compression stage (d). The liquid fraction (6) that is optionally produced can advantageously be mixed with the supply of the distillation stage (g). The compressed gas effluent (7) is then led into a washing stage (e). The waste water effluent (12) is sent into stage (g).

The washed gas effluent (8) is brought into the absorption stage (f), also supplied by an absorbent solution (9). The waste absorbent solution effluent (11) is drawn off from the column before being neutralized or recycled.

The purified gas effluent (10) that is obtained from said stage (f) constitutes the primary product of the process.

The water effluent (13), liquid effluent (4), liquid fraction (6) and waste water effluent (12) are sent into a distillation stage (g) that is shown in the figure by the elements (g1) to (g3). The head (14) is partially condensed in the heat exchanger (g2). This stream is then introduced into the reflux flask (g3) and then separated into a reflux, a vapor distillate (15), and a liquid distillate (16).

The purified water effluent (17) supplies the recycling stage (h). A portion (19) is sent to the washing stage (e) as washing water. The other portion (20) is the dilution water, advantageously recycled to the dehydration stage (a).

The stream (21) shows a possible positioning of the purge.

The following example illustrates the invention without limiting the scope thereof.

EXAMPLE

Figure 2:
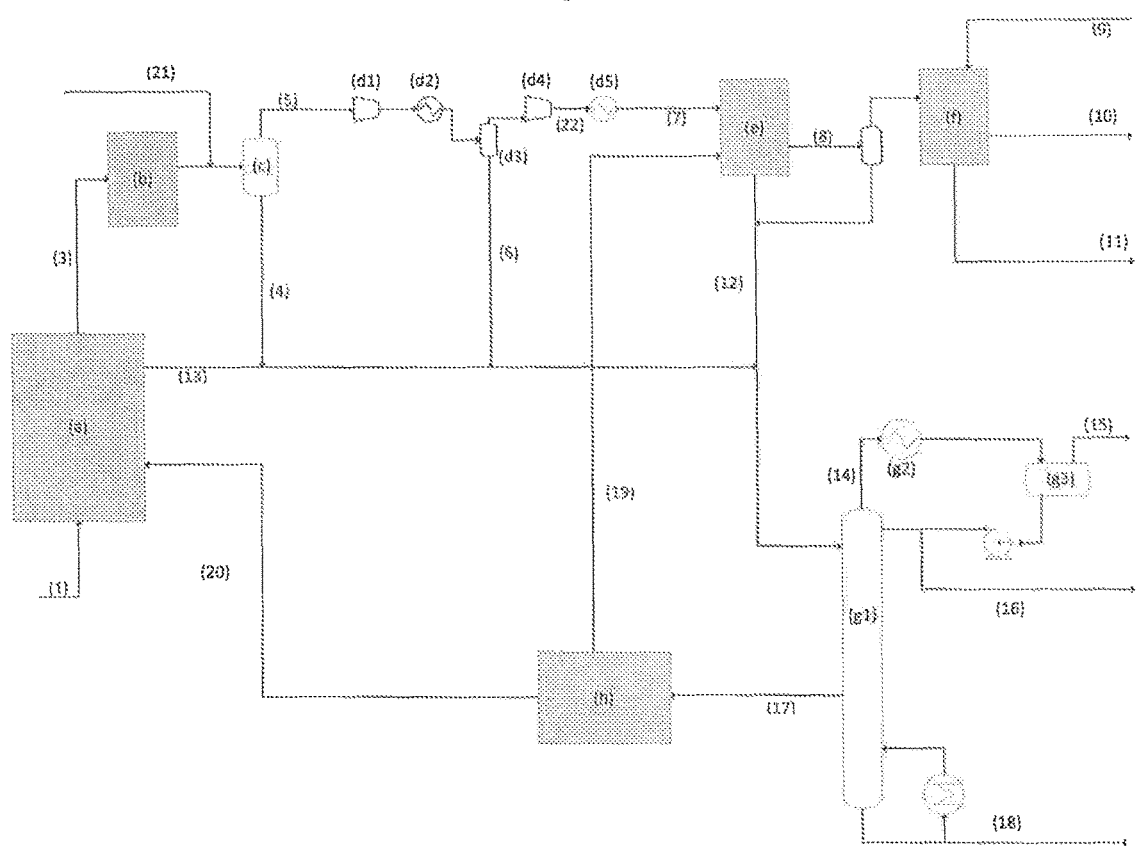

FIG. 2 illustrates the example. The numbering is identical to that of FIG. 1.

FIG. 2 and Table 1 present an example of purification of an ethylene effluent that is obtained from a dehydration stage. The dehydration feedstock consists of an ethanol feedstock (1) in a mixture with 66% by weight of dilution water (20), with the percentage by weight being expressed relative to the total weight of said dehydration feedstock. This dilution makes it possible to limit the drop in temperature due to the endothermy of the reaction. The concentration of $CO_2$ exiting the dehydration reactor is 1,000 ppm by volume.

The ethanol feedstock in question is produced by fermentation of wheat, without extracting glutens, by a dry-milling-type process according to the English term. This feedstock consists of 41,671 kg/h of ethanol in a mixture with 3,993 kg/h of water and 9 kg/h of acetaldehyde. The dehydration feedstock also comprises 103,161 kg/h of dilution water, with said dilution water comprising 3,016 kg/h of unreacted ethanol.

The ethylene effluent (3) of the reaction section is partially condensed in a stage (b), and then neutralized using an aqueous soda solution (21). The pH of the liquid (4) is set at 8.

The compression zone is composed of two stages (d1) and (d4) making it possible to carry out the absorption under a pressure of 13 barg.

The absorption solvent of the $CO_2$ of the column (12) is an aqueous soda solution concentrated to 20% by weight. Its flow rate is 100 kg/h.

The following table provides the primary operating conditions:

TABLE 1

|  |  | Ethanol Feedstock | Stream | | | | | |
|---|---|---|---|---|---|---|---|---|
|  |  |  | 3 | 4 | 5 | 22 | 7 | 8 |
| Temperature | ° C. | 20 | 115 | 35 | 35 | 100 | 35 | 35 |
| Pressure | barg | 2.0 | 2.7 | 2.7 | 2.7 | 13.2 | 12.9 | 12.9 |
| Flow Rates |  |  |  |  |  |  |  |  |
| Total | kg/h | 45,792 | 131,892 | 105,864 | 26,000 | 25,884 | 25,884 | 25,641 |
| Ethanol | kg/h | 41,671 | 2,191 | 2,111 | 79 | 75 | 75 | 38 |
| Water | kg/h | 3,993 | 103,178 | 102,900 | 258 | 148 | 148 | 71 |
| Ethylene | kg/h | 0 | 25,127 | 42 | 25,080 | 25,080 | 25,080 | 25,051 |
| Acetaldehyde | kg/h | 9 | 354 | 267 | 87 | 87 | 87 | 1 |
| CO2 | kg/h | 0 | 132 | 2 | 130 | 130 | 130 | 129 |
| Others (1) | kg/h | 119 | 911 | 542 | 365 | 364 | 364 | 350 |

|  |  | Stream | | | | | | |
|---|---|---|---|---|---|---|---|---|
|  |  | 10 | 13 | 12 | 15 | 16 | 19 | 20 | 18 |
| Temperature | ° C. | 35 | 121 | 36 | 35 | 35 | 35 | 127 | 133 |
| Pressure | barg | 12.6 | 1.4 | 13.1 | 1.6 | 1.6 | 13.2 | 2.2 | 1.9 |
| Flow Rates |  |  |  |  |  |  |  |  |  |
| Total | kg/h | 25,511 | 21,098 | 20,244 | 229 | 227 | 20,000 | 106,742 | 20,194 |
| Ethanol | kg/h | 38 | 870 | 603 | 0 | 10 | 565 | 3,016 | 5 |
| Water | kg/h | 71 | 20,195 | 19,407 | 1 | 8 | 19,330 | 103,161 | 20,173 |
| Ethylene | kg/h | 25,051 | 0 | 29 | 70 | 2 | 0 | 0 | 0 |
| Acetaldehyde | kg/h | 1 | 0 | 86 | 151 | 200 | 0 | 2 | 0 |
| CO2 | kg/h | 0 | 0 | 1 | 2 | 0 | 0 | 0 | 0 |
| Others (1) | kg/h | 350 | 33 | 118 | 4 | 8 | 105 | 562 | 15 |

(1) The term "Others" covers certain minority components with no significant impact on the results, which are not presented in detail for reasons of clarity.

The invention claimed is:

1. Process for the production of ethylene from an ethanol feedstock that comprises at least the following stages:
   a) A stage for dehydration of a dehydration feedstock comprising said ethanol feedstock in such a way as to produce at least an ethylene effluent and at least a water effluent,
   b) A stage for partial condensation of said ethylene effluent by heat exchange with at least a cold source at a temperature of between 20 and 50° C.,
   c) A stage for separation of phases of said partially condensed ethylene effluent in such a way as to produce a gas effluent and a liquid effluent,
   d) A stage for compression of said gas effluent that is obtained from stage b) in such a way as to produce a compressed gas effluent followed by a cooling to a temperature of between 10 and 50° C.,
   e) A stage for washing by bringing said compressed gas effluent into contact with the recycled washing water according to stage h) in a washing column in such a way as to produce a washed gas effluent and a waste water effluent,
   f) A stage for absorption by bringing said washed gas effluent into contact with at least an absorbent solution in an absorption column, with said absorbent solution comprising at least a solvent that is selected from among the group that consists of the chemical and physical solvents, in such a way as to produce a purified gas effluent and a waste absorbent solution effluent,
   g) A stage for distillation of said waste water effluent that is obtained from stage e), and, jointly, said water effluent that is obtained from said dehydration stage in such a way as to produce at least a gas distillate, a liquid distillate, a purified water effluent, and a distillation residue,
   h) A stage for recycling at least a portion of said purified water effluent that is obtained from stage g) upstream from the washing stage e), with said portion then being referred to as washing water.

2. Process according to claim 1, in which said ethanol feedstock is an ethanol feedstock that is produced from a renewable source that is obtained from the biomass.

3. Process according to claim 1, in which said dehydration feedstock also comprises an addition of water that consists of the dilution water that is obtained from the recycling stage h) and/or a stream of water from a source that is external to the process.

4. Process according to claim 1, in which the dehydration feedstock is used as one of the cold sources of said stage b).

5. Process according to claim 1, in which the temperature at the end of stage d) is between 15 and 50° C.

6. Process according to claim 1, in which the temperature at the end of stage d) is between 25 and 45° C.

7. Process according to claim 1, in which the chemical solvents are selected from among soda and the amines are selected from among MEA (monoethanolamine), DEA (diethanolamine), MDEA (methyl diethanolamine), DIPA (diisopropylamine), DGA (diglycolamine), diamines, piperazine, and hydroxyethyl piperazine, taken by themselves or in combination.

8. Process according to claim 1, in which the physical solvents are selected from among N-formyl morpholine, ethers of glycols, sulfolane, and thiodiethanol.

9. Process according to claim 7, in which the physical solvent can be mixed with one or more chemical solvents and/or with water.

10. Process according to claim 1, in which stage g) is implemented in a column with an inside wall.

* * * * *